Figure 1:
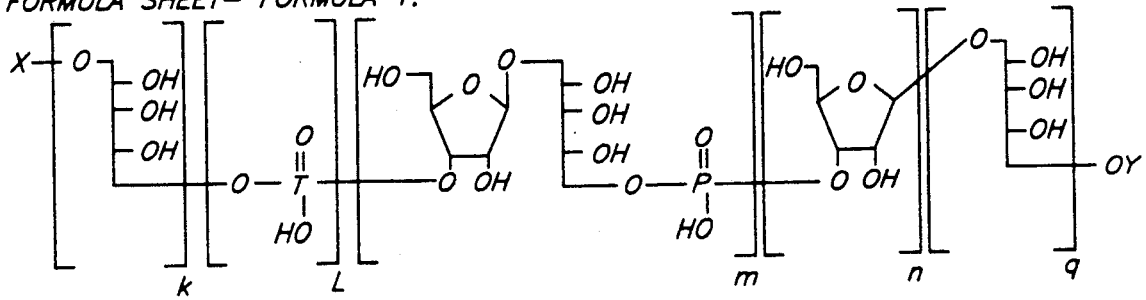
Figure 2:
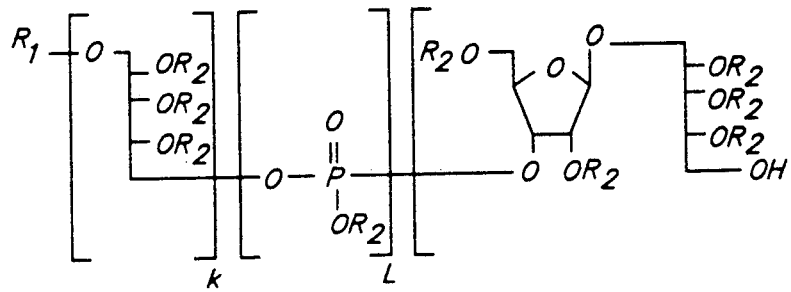
Figure 3:
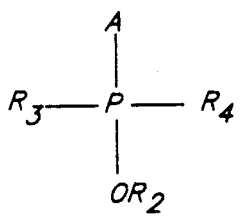
Figure 4:
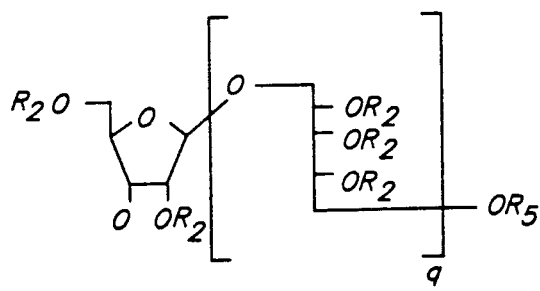
Figure 5:
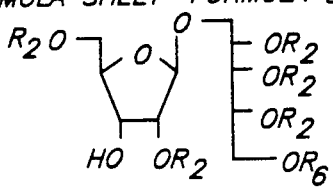
Figure 6:
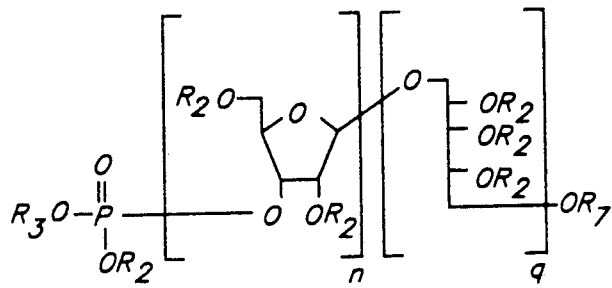
Figure 7:
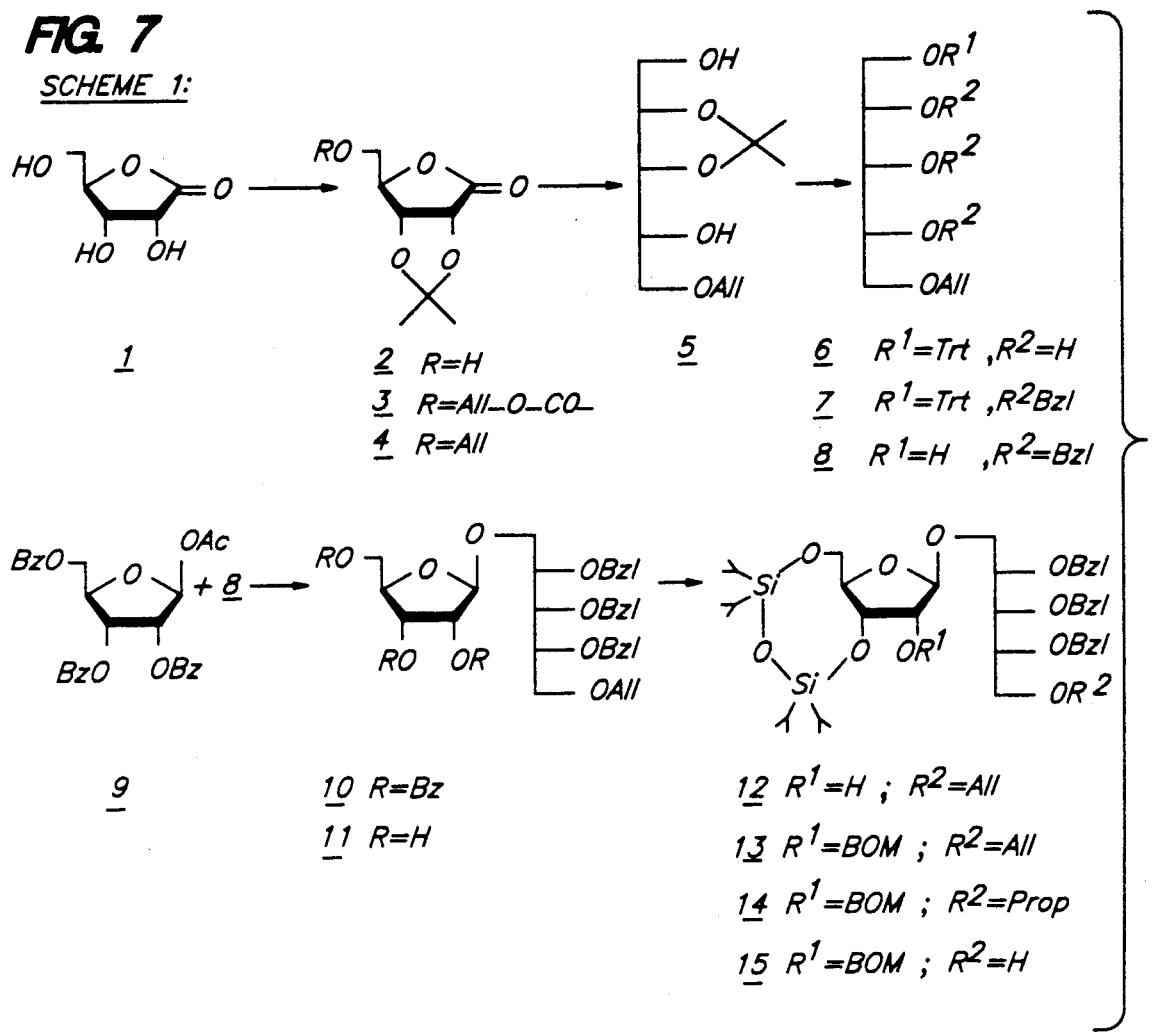
Figure 8:
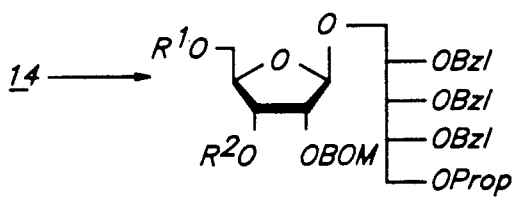
Figure 9:
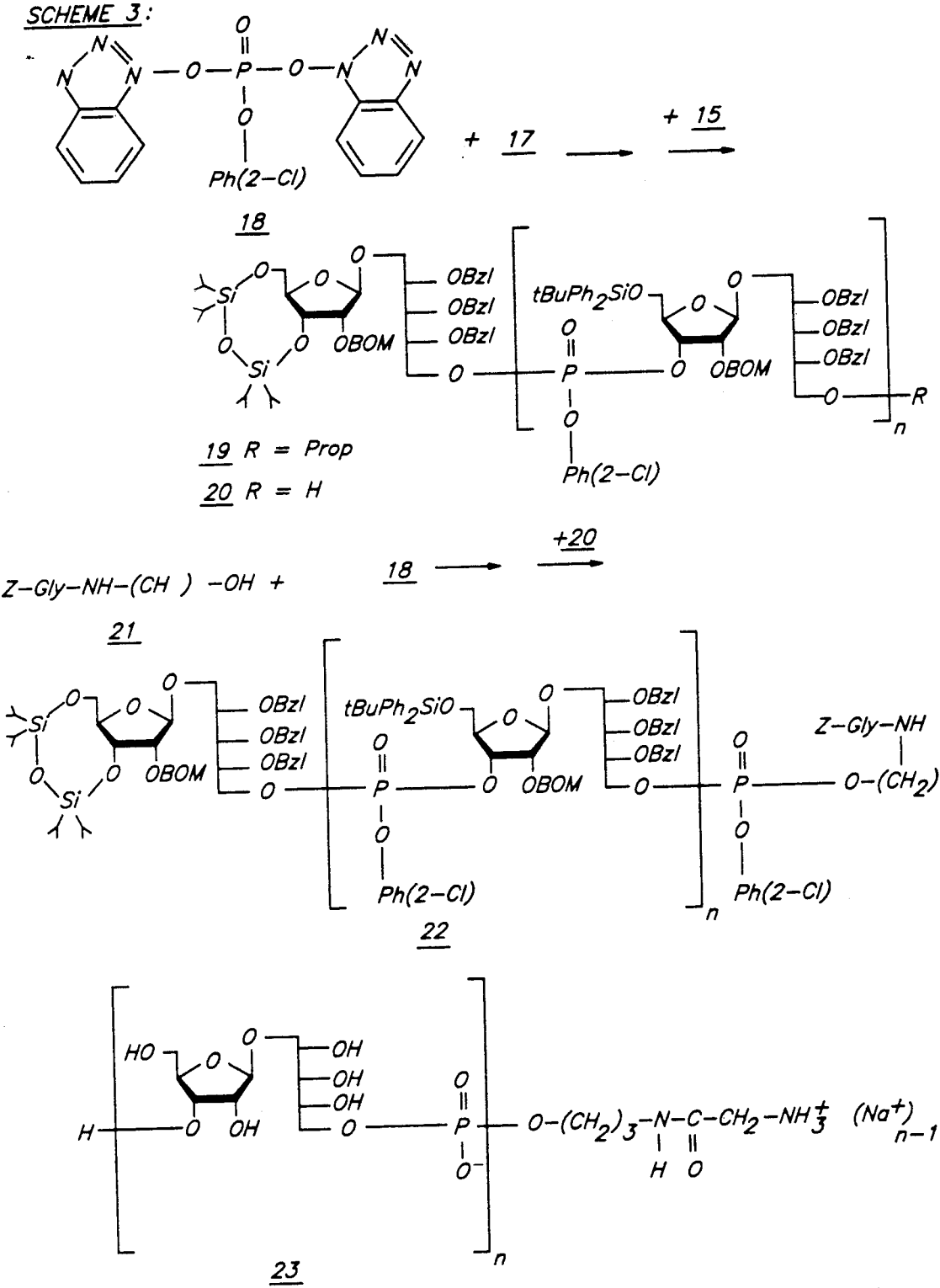
Figure 10:
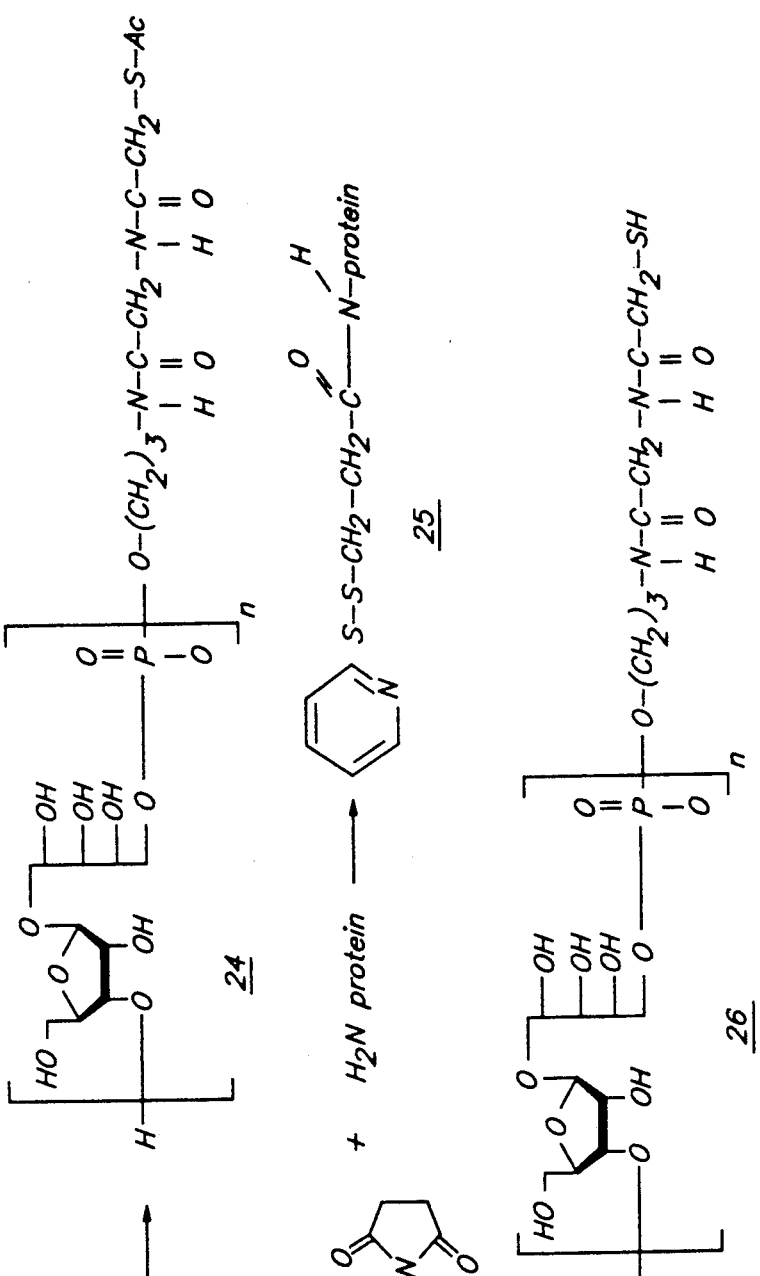

United States Patent [19]

Beuvery et al.

[11] Patent Number: 5,034,519
[45] Date of Patent: Jul. 23, 1991

[54] OLIGOSHACCHARIDES, IMMUNOGENS AND VACCINES, AND METHODS FOR PREPARING SUCH OLIGOSACCHAIDES, IMMUNOGENS AND VACCINES

[75] Inventors: Eduard C. Beuvery, Vianen; Adolf Evenberg, Utrecht; Jan T. Poolman, Broek in Waterland; Jacobus H. van Boom, Voorschoten; Peter Hoogerhout, Gouda; Constant A. A. van Boeckel, Oss, all of Netherlands

[73] Assignee: De Staat Der Nederlanden, Netherlands

[21] Appl. No.: 139,349

[22] Filed: Dec. 29, 1987

[30] Foreign Application Priority Data

Dec. 31, 1986 [NL] Netherlands ............... 86.03325

[51] Int. Cl.$^5$ ............... C07H 13/00; C07H 1/00; C08B 37/00
[52] U.S. Cl. ............... 536/117; 536/1.1; 536/120; 536/124
[58] Field of Search ............... 536/117, 1.1, 120, 124; 514/8, 888, 885, 898; 424/89, 92; 435/101; 530/395, 806, 825

[56] References Cited

U.S. PATENT DOCUMENTS

| | | | |
|---|---|---|---|
| 4,220,717 | 9/1980 | Kuo | 536/1.1 |
| 4,264,764 | 4/1981 | Kniskern et al. | 536/117 |
| 4,451,446 | 5/1984 | Vandevelde et al. | 536/1.1 |
| 4,644,059 | 2/1987 | Gordon | 536/1.1 |
| 4,673,574 | 6/1987 | Anderson | 424/92 |

Primary Examiner—Ronald W. Griffin
Assistant Examiner—Everett White
Attorney, Agent, or Firm—Donna Bobrowicz; William M. Blackstone

[57] ABSTRACT

The invention relates to new oligosaccharides comprising the structure (D-ribose-D-ribitol-phosphate)$_m$, (D-ribitol-phosphate-D-ribose)$_m$ or (phosphate-D-ribose-D-ribitol)$_m$, m being 2,3,4 ... 19 or 20, to immunogens containing such oligosaccharide, to vaccines containing such immunogens and to methods for preparing such oligosaccharides, immunogens and vaccines. The vaccine is very suitable for treating infections caused by Haemophilus influenzae type b.

9 Claims, 4 Drawing Sheets

FORMULA SHEET— FORMULA 1:

FORMULA SHEET— FORMULA 1:

FORMULA SHEET—FORMULA 2:

FORMULA SHEET—FORMULA 3:

FORMULA SHEET—FORMULA 4:

FORMULA SHEET—FORMULA 5:

FORMULA SHEET—FORMULA 6:

SCHEME 1:

SCHEME 2:

16  $R^1=R^2=H$
17  $R^1=tBuPh_2Si-$; $R^2=H$

*All*= allyl; *Trt*= triphenylmethyl; *Bzl*= benzyl; *Bz*= benzoyl;
*Ac*= acetyl; *BOM*= benzyloxymethyl; *Prop*= propen-1-yl;
*tBuPh₂Si-* = t-butyldiphenylsilyl.

SCHEME 3:

Ph(2-Cl) = 2-chlorophenyl; Z= benyzloxycarbonyl;Gly= glycine and the other abbreviations have the same meaning as in Scheme 1 and 2.

SCHEME 4: (Ac= Acetyl)

OLIGOSACCHARIDES, IMMUNOGENS AND VACCINES, AND METHODS FOR PREPARING SUCH OLIGOSACCHARIDES, IMMUNOGENS AND VACCINES

The invention relates to new oligosaccharides containing D-ribose, D-ribitol and phosphate units, to immunogens containing such oligosaccharides, to vaccines containing such immunogens and to methods for preparing such oligosaccharides, immunogens and vaccines.

The capsular polysaccharide of the bacterium *Haemophilus influenzae* type b consists of many units of D-ribose-D-ribitol-phosphate (→3)-D-ribf-(1→1)-ribotol-5→PO$_4$-). *Haemophilus influenzae* type b is, inter alia, a pathogenic bacterium that causes meningitis and other infectious diseases.

It has been found that immunity can be obtained by administration of the capsular polysaccharide of *Haemophilus influenzae* type b (HIB). It has also been found that, in particular in children under 2 years old, the immunity obtained is of short duration and in children under 18 months old it cannot be detected at all. This can be improved by administering the capsular polysaccharide associated with a so-called thymus-dependent carrier (protein). Such polysaccharide-protein conjugates have the disadvantage that the structure is not accurately defined and that the polysaccharide-part in the product is not homogeneous. This has the result that every freshly prepared batch of vaccine which contains such conjugates has to be tested in experimental animals and/or humans in relation to the effectiveness of the vaccine. In addition, the use of such a product in a vaccine may produce undesirable antibodies or toxicity.

Oligosaccharides obtained by degradation of the capsular polysaccharide HIB are not pure as well, although better defined. Here, too, the effectiveness will always have to be tested again.

There is therefore the need for a vaccine against HIB disease containing an accurately described, pure oligosaccharide fragment, i.e. an oligosaccharide fragment which does not contain oligosaccharides having a different structure or chain length.

It has now been found that such pure oligosaccharides can be obtained by a synthetic route and that suitable immunogens can be obtained by associating such fragments with a carrier. Such immunogens can be used in vaccines. The fact that such an oligosaccharide can be prepared by a synthetic route has also the advantage that the availability is not dependent on the availability of the pathogenic bacterium HIB.

The invention therefore relates to oligosaccharides which comprise D-ribose-D-ribitol-phosphate, D-ribitol-phosphate-D-ribose or phosphate-D-ribose-D-ribitol 2,3,4 ... 19 or 20 times and in particular to oligosaccharides having the formula:

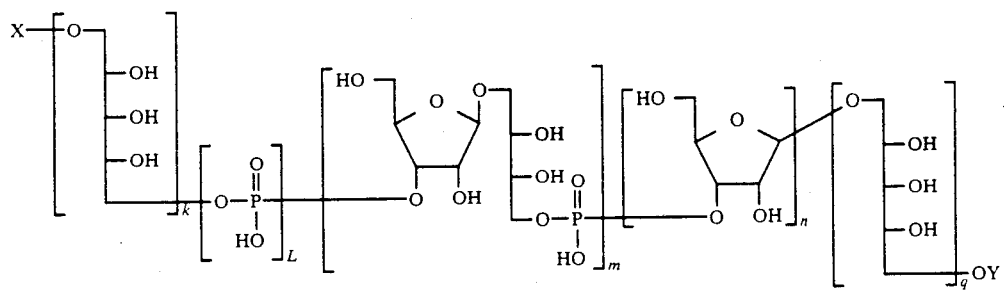

(formula I)

wherein
k=0 or 1 if L=1,
k=0 if L=0,
L=O or 1
m=2,3 ... 19 or 20, provided that m may be 1 if k, L and n=1 or if L, n and q=1,
n=0 or 1,
q=0 or 1 if n=1,
q=0 if n=0,
X=hydrogen, a reactive group which is capable of forming, directly or indirectly, a bond with a carrier, or a group having a hydrophobic chain at the unbonded end, or the terminal XO— group is replaced by the reactive group H$_2$N— or HS—, and
Y=hydrogen, a reactive group which is capable of forming, directly or indirectly, a bond with a carrier, or a group with a hydrophobic chain at the unbonded end, or the terminal —OY group is replaced by the reactive group —NH$_2$ or —SH, provided that Y=hydrogen if X≠hydrogen or that X=hydrogen if Y≠hydrogen,
and salts thereof.

The invention also relates to immunogens containing an oligosaccharide as described above, which oligosaccharide is associated with a carrier, or containing an association of several molecules of an oligosaccharide as described above, and to vaccines which contain such immunogens.

The invention also relates to methods for preparing the oligosaccharides, the immunogens and the vaccines according to the invention.

Disregarding X(XO—) and Y(—OY), the D-ribose-D-ribitol-phosphate skeleton as shown in formula 1 may end, both on the left and on the right, in a ribose, a ribitol or a phosphate group. Oligosaccharides which, disregarding X(XO—) and Y(—OY), end in a ribitol or ribose group on the left and in a phosphate group on the right, or in ribitol or ribose group on the right and in a phosphate group on the left are, however, preferred. Preferably, m is equal to 2,3,4,5 or 6 since an oligosaccharide skeleton with such a length is in general already adequate in relation to the object in view. With still greater preference, m is equal to 3,4,5 or 6.

Preferably, k, L, n and q are equal to zero, X is equal to H and Y is not equal to H.

Because the phosphate groups in the oligosacchrides according to the invention occur in the ionized state in solution at, for example, neutral pH, the oligosaccharides according to the present invention are prepared preferably in the form of a salt, for example a sodium salt.

because the oligosaccharides according to the present invention do not per se have any immunogenicity, or inadequate immunogenicity, it is necessary to associate said oligosaccharides with a carrier, as a result of which said immunogenicity is in fact obtained to a sufficient degree. Depending on the type of carrier, the manner in which the oligosaccharide is associated with the carrier will vary. The association of the oligosaccharide and the carrier proceeds directly or indirectly via X(XO—) or Y(—OY) in formula 1.

If X and Y are hydrogen, the oligosaccharide will have to be modified at one of those sites to make association with the carrier possible. Because the —OH and =O groups shown in formula 1, which are active to a greater or lesser degree, are protected for a longer or shorter time during the preparation of the oligosaccharides according to the invention, it is advantageous to introduce the modifications required for association with the carrier before the protecting groups are removed. As already stated, the association of the oligosaccharide with the carrier takes place either via X(XO—) or via Y(—OY). Now if X and Y were hydrogen in formula 1, the protecting groups would have to be introduced again before the group required for association with the carrier could be introduced. X is therefore preferably equal to hydrogen and Y(—OY) equal to one of the other groups specified or Y is equal to hydrogen and X(XO—) equal to one of the other groups specified.

Hereinafter, if "X" or "Y" or the term "reactive group" is used, the case is also meant in which the reactive group consists of the reactive group —NH$_2$ or —SH, it being necessary to read —NH$_2$ or —SH for XO— or —OY respectively. The oligosaccharide according to the present invention therefore ends preferably at one end in a hydroxyl group and at the other end in a reactive group or a group having a hydrophobic chain at the unbonded end. The choice between these two types of group is determined by the manner in which the association of the oligosaccharide and the carrier is achieved. In principle, two methods known per se are available for this purpose. According to the first method, the oligosaccharide is bonded to the carrier. In that case, the carrier is usually a protein. According to the second method, the association of the oligosaccharide is obtained by a hydrophobic interaction between a group bonded to the oligosaccharide having a hydrophobic chain at the unbonded end and the carrier, the carrier being a micelle, a vesicle or a liposome, or by a hydrophobic interaction of the oligosaccharides among themselves. In the first case the hydrophobic group enters into a hydrophobic interaction with the hydrophobic regions of the amphiphilic compounds (lipids) in the micelle, the vesicle or the liposome, while the oligosaccharide finishes up at the interface of the micelle, the vesicle or the liposome.

Reactive groups which are capable of forming, directly or indirectly, a bond with a protein are known. By an indirect bond in this connection is meant that the bond is brought about between the reactive group and the protein by means of an additional compound. If X or Y in formula 1 is a reactive group, all the reactive groups are in principle suitable which are capable of forming a bond with a carboxyl, amine or another, optionally introduced reactive function of the protein or which can be bonded by means of an additional compound to a carboxyl, amine or other, optionally introduced reactive function of the protein.

Examples of such reactive groups are groups having the following reactive function:

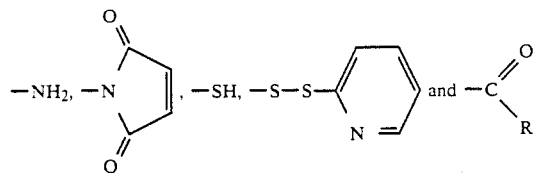

where R=—OH, —N$_3$, —O—alkyl(C$_{1-12}$), —OC$_6$F$_5$, —H, —Br, —Cl or

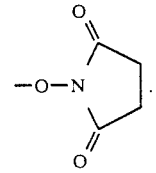

The reactive group may consist of one of these reactive functions or, if the reactive group is larger, may contain one of said reactive functions, in which case the group preferably ends in one of the said reactive functions.

Because it is of advantage in promoting the immunogenicity if the ribose-ribitol-phosphate units in the oligosaccharide are at some distance from the protein after bonding the oligosaccharide to the protein, the reactive group is preferably a fairly long group with one of the abovementioned reactive functions.

As stated, a reactive group is incorporated at the end of the oligosaccharide skeleton preferably when said skeleton is still protected. Once a reactive group containing one of the said reactive functions has been incorporated, said reactive function can be converted into one of the other reactive functions if the oligosaccharide skeleton is still protected, but also if the skeleton is already completely deprotected.

Thus, reactive groups containing an —NH$_2$ function, such as

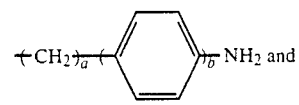

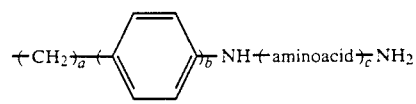

where a=0-16, b=0-2, c=1-10 and the terminal amino acid is preferably glycine, can, by means of a compound containing an active ester and a maleimide function, be converted into a reactive group containing a maleimide function (said groups yield, with

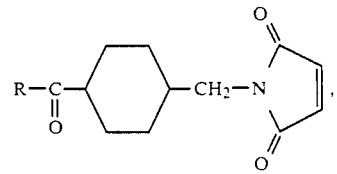

where R has the same meaning as previously defined, the groups

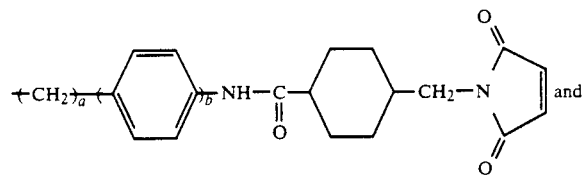

and

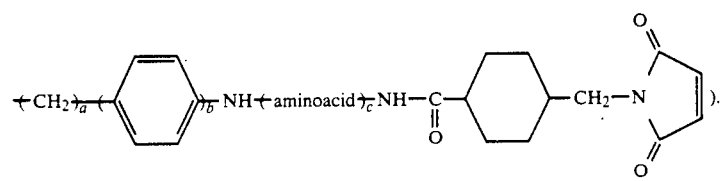

Furthermore, reactive groups containing an —NH$_2$ function can be converted by means of a compound containing two active ester or aldehyde functions into a reactive group containing an active ester or aldehyde as the reactive function, for example,

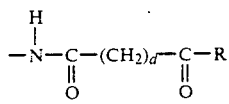

where R has the same meaning as previously defined and d = 1-6, or by means of a compound containing an active ester and an —SH function into a reactive group containing an —SH function, for example,

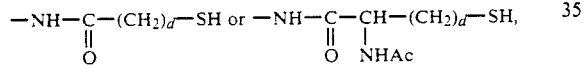

where d = 1-6 and Ac = acetyl.

Reactive groups containing an —SH function can be converted by means of a compound containing an active ester and a maleimide function into a reactive group containing an active ester as the reactive function, for example,

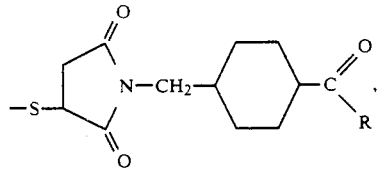

Reactive groups containing a

group as the reactive function can be converted by reaction with compounds containing a —NH$_2$ and —SH function or a maleimide and —NH$_2$ function into a reactive group containing respectively a —SH or maleimide group as the reactive function.

Such conversions of the reactive group are known per se in the literature.

The thus prepared oligosaccharides according to the invention are bonded to a protein or peptide. Reactive —NH$_2$, —COOH or —SH groups in the protein can be converted into one of the other reactive groups described above by a procedure analogous to those described there.

The oligosaccharide according to the invention and the protein can then be bonded to each other, inter alia, as follows:

oligosaccharide — maleimide + HS-protein ⟶ immunogen oligosaccharide — SH + maleimide-protein ⟶ immunogen oligosaccharide — SH +

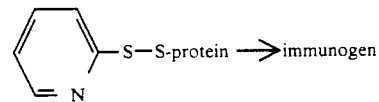

oligosaccharide — S—S

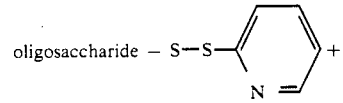

+

HS-protein ⟶ immunogen

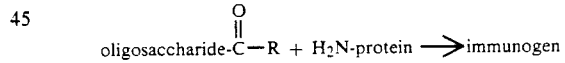

oligosaccharide-NH$_2$ +

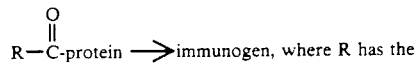

⟶ immunogen, where R has the same meaning as previously defined. Such couplings can be brought about directly or indirectly.

Furthermore, oligosaccharides with a reactive —NH$_2$ function can, for example, be coupled to an NH$_2$ group of a protein by means of a coupling agent, such as bis[N-hydroxysuccinimide] esters or glutaric dialdehyde.

If X or Y in formula 1 is a group containing a hydrophobic chain at the unbonded end those groups are suitable for this purpose which are capable of entering into a hydrophobic interaction with a micelle, a vesicle or liposome or are capable of forming a micelle by means of hydrophobic interactions.

The hydrophobic chain is preferably an alkyl group containing 12-24 carbon atoms. Greatest preference is given to groups in which the alkyl group containing 12-24 carbon atoms forms said group.

Still more preferably, the group is an unbranched alkyl group containing 14-22 carbon atoms.

The oligosaccharides according to the present invention can appropriately be used for producing a vaccine against HIB disease. Since the oligosaccharides according to the present invention are not immunogenic per se, they should be associated with a carrier which imparts immunogenicity to the associate. This principle is known per se in so-called haptens which, although not immunogenic per se, can be rendered immunogenic by associating them with a carrier. Suitable carriers are proteins, peptides, micelles, vesicles and liposomes. The greatest preference is given to proteins or micelles.

A especially suitable proteins and peptides, mention may be made of tetanus toxin, tetanus toxoid, diptheria toxin, diptheria toxoid, pertussis toxin, pertussis toxoid, pertussis filamenteous haemagglutinine, pertussis fimbriae, pertussis outer-membrane proteins, meningococci (*Neisseria meningitidis*) outer-membrane proteins, *Haemophilus influenzae* outer-membrane proteins, *Haemophilus influenzae* fimbriae, polio virus sub-unit proteins and measles virus sub-unit proteins. Proteins of *Haemophilus influenzae* are most preferred. An advantage of such carriers is that they are or can be used in existing DPTP vaccines. The said proteins are known per se, as are methods of isolating such proteins. Methods are also known of associating saccharides with such proteins. Usually a covalent bond between the saccharide and the protein is involved.

If X or Y in formula 1 is a group containing a hydrophobic chain at the unbonded end, the oligosaccharide can be rendered immunogenic in an appropriate manner by associating said oligosaccharide with micelles, vesicles or liposomes. The association is obtained by a hydrophobic interaction of the hydrophobic chain with hydrophobic parts of the micelle, the vesicle or the liposome. Such association methods are known per se.

If X or Y in formula 1 is a reactive group, a reaction may optionally be carried out first with a compound containing a reactive group and a hydrophobic chain. The product thus obtained can then be associated with micelles, vesicles or liposomes.

Another method of imparting immunogenicity to the oligosaccharides according to the invention is to treat oligosaccharides in which X or Y is a group containing a hydrophobic chain at the unbonded end in a manner such that said hydrophobic chains form a micelle structure by means of hydrophobic interactions. In this case, the immunogenicity is not obtained by an association of the oligosaccharide with a carrier but by association of several molecules of said oligosaccharide with each other.

Yet another possibility of preparing an immunogen is to couple the oligosaccharides according to formula 1 in which X or Y is a reactive group to an amphiphilic adjuvant molecule by means of a covalent bond via said reactive group. This coupling may be direct or indirect. After coupling the oligosaccharide and the adjuvant, the unbonded end of the adjuvant can form a micelle, possibly together with an unbonded adjuvant or with other lipid substances. Suitable amphiphilic adjuvants are, for example avridine (N,N-dioctadecyl-N',N'-bis(2-hydroxyethyl)propanediamine), the lipoidal amine 4-aminomethyl-1(2,3-(di-n-decyloxy)-n-propyl)-4-phenyl-piperidine, dimethyl-dioctadecylammonium bromide, laurylmuramyl dipeptide, lauryl tetrapeptide, (N²-[N-(N-lauryl-L-alanyl)-γ-D-glutamyl]-N⁶-(glycyl)-D,D-L,L-2,6-diamino pimelic acid, L-tyrosine and alkyl derivatives thereof, maltose tetrapalmitate, pluronic polyols, L-tyrosine azobenzene-p-arsonate, sorbitan monooleat (Span 80), trehalose derivatives (such as trehalose dimycolate), retinoylic acid and derivatives thereof, D,L-α-tocopherol (vitamin E), lipid A and analogues and glycosides, such as, for example, saponines (for example, Quil A from the bast of *Quillaja saponaria* Molina).

Such immunogens and methods for preparing these immunogens are known per se from the European Patent Application 86,200,203.7. Lipid A and analogues are known as adjuvants from the Dutch Patent Application 8,500,499. The use of saponines as adjuvants and the micelle formation of saponines coupled to antigen determinants is known from the Dutch patent Application 8,303,646.

The immunogens according to the present invention may appropriately be used in the preparation of a vaccine against HIB disease. The improve the immunogenicity further, adjuvants can be used with advantage. The use of such adjuvants and said adjuvants are known per se. The adjuvants can be added to the immunogen. It is also possible to associate adjuvants with the immunogen. Such methods of improving the immunogenicity are also known per se. The immunogens according to the present invention thus comprise, in addition to the associations of oligosaccharides with carriers and the associations between oligosaccharides themselves, also association of said two types with which an adjuvant is also associated.

The vaccine according to the present invention contains at least immunogens according to the present invention. Usually, the immunogen will be in the vaccine in an aqueous solution, emulsion or suspension, in which additions which are usual for vaccines may occur, such as adjuvants, stabilizers, buffers and other immunogens. Suitable adjuvants which may be added are aluminium hydroxide, phosphate or oxide or a composition which consists of a mineral oil, for example Marcol 52, or a vegetable oil and one or more emulsifying agents, such as Tween 80 or Span 80, or one of the amphiphilic adjuvants already mentioned above.

Suitable stabilizers are carbohydrates such as sorbitol, lactose, mannitol, starch, dextran and glucose or proteins such as albumin or casein.

As buffers it is possible to use, for example, an alkali metal phosphate, an alkalimetal carbonate or an alkaline earth metal carbonate buffer.

As already staged, the vaccine may also contain other immunogens. In that case, a so-called cocktail is involved which has the advantage that immunity against several pathogens can be obtained by a single administration. Other immunogens which may be used are, for example, the immunogens used in the known DPTP vaccines. The vaccine is prepared according to methods known per se by using an immunogen according to the present invention, e.g. by dissolving, emulgating or suspending the immunogen in an aqueous environment. One or more of the usual additives may be added to or may be present in said aqueous environment.

Such a vaccine can be used for immunizing against HIB disease, but also for so-called "priming" (in which the body is not directly stimulated to form specific free antibodies but is in fact preconditioned so that, after subsequent infection or revaccination, a strong immune reaction is provoked). The vaccine is usually administered by means of intramuscular or subcutaneous injection. In general, the quantity of immunogen administered per injection will be between 0.1 and 100 μg per dose.

The vaccine according to the present invention offers, in principle, protection for every individual against HIB disease and is extremely suitable for vaccinating young children (under 2 years old) in particular. As a result of the purity of the oligosaccharide according to the present invention, it is not necessary to test every batch prepared of the vaccine containing such an oligosaccharide again for its effectiveness. In addition, the quantity of undesirably stimulated antibodies, the occurence of other side-effects, like toxicity, are limited with such a vaccine.

The oligosaccharides according to the present invention can be prepared by reacting several compounds selected from the group consisting of compounds which contain ribose, ribose-ribitol, ribose-ribitol-phosphate, ribitol, ribitol-phosphate, ribitol-phosphate-ribose, phosphate, phosphate-ribose and phosphate-ribose-ribitol units, where said units are provided with the necessary protecting groups, with each other in several steps and finally removing the protecting groups. The oligosaccharides according to the present invention are ultimately prepared by replacing the protective groups in oligosaccharides, comprising the structure (D-ribose-D-ribitol-phosphate)$_m$, (D-ribitol-phosphate-D-ribose)$_m$ or (phosphate-D-ribose-D-ribitol)$_m$, wherein m=2,3,4 ... 19 or 20 and wherein the hydrogen atom in the free hydroxy groups has been replaced by a protective group, by a hydrogen atom. In its generality, it is known that oligosaccharides can be prepared by bonding larger or smaller units, of which the final oligosaccharide is constructed, to each other by means of several reactions, the units being provided with the necessary protecting groups. After the desired oligosaccharide has been constructed, the protecting groups are removed. If one of the groups X and Y in formula 1 according to the formula sheet is not hydrogen and these groups did not occur in the compounds from which the oligosaccharide has been constructed, these groups should also be incorporated before the protecting groups are removed.

The oligosaccharides according to the present invention can be prepared starting from a compound having formula 2 according to the formula sheet. Starting from this compound there are a number of methods of preparing the oligosaccharides according to the invention.

The first method is to construct the oligosaccharide by continuously incorporating a small unit. This can be done by phosphorylating compounds having formula 2 with compounds having formula 3, then coupling a compound with formula 5 to the phosphor group, repeating these two steps as often as desired and finally terminating the construction by reaction with a compound having formula 6 according to the formula sheet, after which the protecting groups are still to be removed. Another way is to phosphorylate a compound having formula 5 with a compound having formula 3, bonding the product obtained by means of the phosphorus group to a compound having formula 2, to repeat this step as often as desired, and finally to terminate the construction by reaction with a compound having formula 6 according to the formula sheet, after which the protecting groups are still to be removed. The invention therefore relates in particular to a method for preparing the oligosaccharides according to the present invention, characterized in that 1) a compound having formula 2 according to the formula sheet is reacted with a compound having formula 3 according to the formula sheet, in which formulae, k=0 if L=0,
k=0 or 1 if L=1,
L=0 or 1,
$R_1$ = a permanently protecting group, a reactive group which is capable of forming, directly or indirectly, a bond with a carrier and which contains a reactive function which is provided with a permanently protecting group, or a group containing a hydrophobic chain at the unbonded end, or the terminal group $R_1O$— is replaced by the reactive group $H_2N$—° or HS—, which reactive group is provided with a permanently protecting group,
$R_2$ = a permanently protecting group,
A = an oxygen atom bonded by means of a double bond to the phosphorus atom or nothing (in this case the phosphorus atom has a free electron pair),
$R_3$ = a reactive group, and
$R_4$ = a reactive group or a group having formula 4 according to the formula sheet in which q=0 or 1,
$R_2$ = a permanently protecting group, and $R_5$ = a permanently protecting group, a reactive group which is capable of forming, directly or indirectly, a bond which a carrier and which contains a reactive function which is provided with a permanently protecting group, or a group with a hydrophobic chain at the unbonded end, or the terminal group —$OR_5$ is replaced by the reactive group $H_2N$— or HS—, which reactive group is provided with a permanently protecting group, and that 2) if $R_4$ is not a group having formula 4, the product obtained in step 1) is reacted with a compound having formula 5 according to the formula sheet where $R_2$ is a permanently protecting group and $R_6$ is a temporarily protecting group, and the product thus obtained is deprotected by replacing $R_6$ by a hydrogen atom, and that 3) step 2) is repeated m-2 times with the product obtained in step 2) instead of the product obtained in step 1), and that 4) the product obtained from step 2) or step 3) is reacted with a compound having formula 6 according to the formula sheet where
$R_2$ = a permanently protecting group,
$R_3$ = a reactive group,
$R_7$ = a permanently protecting group, a reactive group which is capable of forming a bond, directly or indirectly, with a carrier and which contains a reactive function which is provided with a permanently protecting group, or a group with a hydrophobic chain at the unbonded end, or external group $R_7O$— is replaced by the reactive group $H_2N$— or HS—, which reactive group is provided with a permanently protecting group,
n=0 or 1,
q=0 if n=O,
q=0 or 1 if n=1, and that 5) in the product thus obtained the permanently protecting group $R_1$ or $R_7$, if present and if desired, is replaced by X or Y insofar as X or Y is not hydrogen, and that 6) the compound obtained in step 1), 4) or 5) is deprotected by replacing the permanently protecting groups by a hydrogen atom.

The invention also relates to a method for preparing oligosaccharides according to the present invention characterized in that 1) a compound having formula 2 according to the formula sheet, in which k, L, $R_1$ and $R_2$ have the same meaning as above, is reacted with the reaction product of a compound having formula 3 according to the formula sheet, in which $R_2$, $R_3$ and $R_4$ have the same meaning as above, with the proviso that $R_4$ is not a group having formula 4 according to the formula sheet, and of a compound having formula 5 according to the formula sheet, in which $R_2$ and $R_6$ have the same meaning as above, and the product thus obtained is deprotected by replacing $R_6$ by a hydrogen atom, and that 2) the product obtained in step 1) is reacted with the reaction product of a compound having formula 3 and a compound having formula 5 according to the formula sheet and the so obtained product is deprotected by replacing $R_6$ by a hydrogen atom and that this procedure is repeated m-3 times with the product obtained, and that 3) the product obtained in step 1) or 2) is reacted with a compound having formula 6 according to the formula sheet, in which n, q, $R_2$, $R_3$ and $R_7$ have the same meaning as above, and that 4) in the product thus obtained, the permanently protecting group $R_1$ or $R_7$, if present and if desired, is replaced by X or Y insofar as X or Y is not hydrogen, and that 5) the compound obtained in step 3) or 4) is deprotected by replacing the permanently protecting groups by a hydrogen atom.

$R_1$ may be a permanently protecting group or, if X in the desired oligosaccharide is not hydrogen, may be the same as X, with the proviso that the reactive function is provided with a permanently protecting group, as a result of which the reactive function does not enter into any reaction during the formation of the oligosaccharide skeleton. Since X in formula 1 is preferably hydrogen, $R_1$ is preferably a permanently protecting group.

$R_2$ is a permanently protecting group $R_3$ in formula 3 is a reactive group and $R_4$ is a reactive group or a group having formula 4. Since Y is preferably not equal to hydrogen, $R_5$ in formula 4 is preferably a group other than a permanently protecting group. Since k, L, n and q are preferably zero, $R_4$ is preferably a reactive group and therefore not a group having formula 4.

By the term "permanently protecting group" is meant groups which during the whole course of the preparation of the oligosaccharides according to the invention exert their protecting influence on the—otherwise—reactive groups. Only after the synthesis has been completely carried out, are the permanently protecting groups removed by replacing them with a hydrogen atom. Such protecting groups are known in sugar and nucleotide chemistry.

The groups $R_2$ in formula 2, 3, 4, 5, and 6 may be the same or different groups, preferably chosen from the following set of groups: benzoyl, benzyl, benzyloxymethyl, 2-chlorophenyl, benzyloxycarbonyl, tert.butyldiphenylsilyl, alkyl containing 10-20 carbon atoms, tetrahydropyranyl, tert.butyldimethylsilyl and trityl. Preferably, $R_2$ in the ribitol units is benzyl.

If $R_1$ or $R_5$ are or contain permanently protecting groups, said groups may appropriately be chosen from the abovementioned set. The same applies to $R_2$ in formula 3, which is preferably 2-chlorophenyl.

Preferably $R_1$ in formula 2, together with $R_2$ at position 5' of the ribose unit forms a group

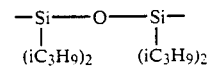

(in that case, k and L are equal to zero) or $R_2$ at position 5' of the ribose unit and $R_1$ are benzyl.

Preferably, $R_2$ at position 2' in the ribose unit is benzyl, benzyloxymethyl, tetrahydropyranyl or tert.butyldimethylsilyl, benzyl and benzyloxymethyl being most preferred, and $R_2$ in position 5' in the ribose unit in formula 4, 5 and 6 is benzyl, benzyloxymethyl, tetrahydropyranyl, trityl or tert.butyldiphenylsilyl, with benzyl and tert.butyldiphenylsilyl being most preferred.

The reactive groups $R_3$ and $R_4$ in formula 3 may be groups which are together capable of bringing about a bond between the free OH group in compounds having formula 5 and formula 2. Suitable compounds having formula 3 are:

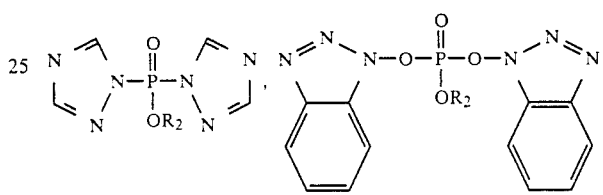

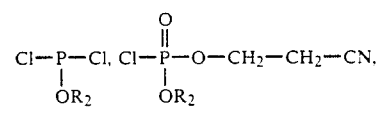

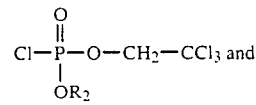

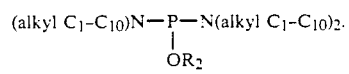

The reaction between compounds having formula 2 and 3 usually takes place at atmospheric pressure and a temperature between 0° and 60° for 20 min. -3 hours.

Then the product thus obtained is reacted with a compound having formula 5 in which $R_2$ is a permanently protecting group and $R_6$ is a temporarily protecting group.

In relation to $R_2$, the same applies as has already been noted above in discussing formula 2. A temporarily protecting group means in this connection that a group is used which exerts its protecting function during a part of the construction of the oligosaccharide skeleton in order subsequently, before the construction is completely finished, to be selectively removed, i.e. without the permanently protecting groups being removed. Such groups are known in sugar and nuceleotide chemistry. Suitable groups are: allyl, 1-propenyl, dimethoxytrityl, chloroacetyl, bromoacetyl, levulinoyl and allyloxycarbonyl. The greatest preference for $R_6$ is for allyl and 1-propenyl.

The reaction with the compound having formula 5 usually takes place at atmospheric pressure and a temperature between 0° and 60° C. for 20 min.-3 hours.

After reaction with the compound having formula 5, group $R_6$ is selectively removed, usually at atmospheric pressure and a temperature of 0° to 60° C. for 10°-60 min., and replaced by a hydrogen atom.

Then, if desired, the reaction with a compound according to formula 3, provided $R_4$ is a reactive group, the reaction with a compound according to formula 5 and the replacement of $R_6$ by a hydrogen atom can be repeated m-2 times. The conditions under which these steps are performed are the same as for the equivalent steps already described above.

Then the product obtained is reacted with a compound according to formula 6 according to the formula sheet. In relation to $R_2$ and $R_3$, the same applies as has already been noted above in relation to $R_2$ and $R_3$ in the discussion of the formulae 2 and 3. Preferably, n and q are equal to zero. $R_7$ has the same meaning as $R_1$; this does not means that $R_1$ and $R_7$ are necessarily identical. Since Y in the desired oligosaccharide is preferably not hydrogen, $R_7$ is preferably equal to Y (Y≠H), with the proviso that the reactive function is provided with a permanently protecting group. Groups which can appropriately be used for this purpose are the permanently protecting groups already mentioned; the greatest preference is given to the benzyloxycarbonyl group.

The conditions under which the reaction with a compound according to formula 6 usually takes place are as follows: temperature 10°-60° C. at atmospheric pressure, time 15 min.–6 hours.

The construction of the oligosaccharide skeleton is thereby complete. If desired, $R_1$ or $R_7$, in so far as $R_1$ or $R_7$ is a permanently protecting group, can now be replaced by X or Y insofar as X or Y≠H. In the oligosaccharides according to the present invention, X is preferably hydrogen; in that case, $R_1$ is preferably a permanently protecting group. Since Y is preferably not hydrogen, $R_7$ is preferably the same as Y (Y≠H) provided with a permanently protecting group. In that case, neither $R_1$ nor $R_7$ needs to be replaced by X or Y insofar as X or Y≠H. Preferably, this step is therefore not performed.

Finally, the permanently protecting groups are replaced by a hydrogen atom. Just as the use and the introduction of permanently protecting groups is known in sugar and nucleotide chemistry, deprotection is also known.

However, the preparation of oligosaccharides according to the present invention, in which k, L, n and q=0, is preferably performed by allowing a compound having formula 2 to react with the reaction product of a compound according to formula 3 and according to formula 5. After deprotecting the product obtained by removing $R_6$, the oligosaccharide skeleton can be extended further by reaction with the product of a compound according to formula 3 and according to formula 5 and deprotecting the product obtained again by removing $R_6$. This can be repeated as often as desired bearing in mind the required length of the oligosaccharide skeleton. The construction of the oligosaccharide skeleton is terminated by reaction with a compound according to formula 6. The advantage of this approach is that the number of steps can be reduced because the product, obtained by reacting a compound having formula 3 and 5, needs to be prepared only once. A second advantage is the fact that a compound having formula 3 reacts more selectively with a compound according to formula 5 than with a compound according to formula 2. In both cases, the compound having formula 3 serves to bond only one compound having formula 2 or 5, while the other reactive group of the compound having formula 3 remains intact. In the case of reaction with a compound according to formula 2, more undesirable dimer formation occurs.

The reaction between a compound having formula 3 and 5 is performed at a temperature between 10° and 60° C. and at atmospheric pressure and in general will be complete within 10–60 min. The product thus formed is reacted also at 10°-60° C. and atmospheric pressure with a compound according to formula 2. This reaction will in general be complete after 0.5-3 hours and is preferably performed in the presence of a catalyst, such as N-methylimidazole or tetrazole, or after activation with or in the presence of an activating reagent, such as 1-(2,4,6-triisopropylbenzene-2'-sulphonyl)-3-nitro-1,2,4-triazole or 1-(mesitylene-2'-sulphonyl)-3-nitro-1,2,4-triazole.

Compounds according to formula 3 which can appropriately be used are in principle the same as the compounds already mentioned above.

The oligosaccharides according to the present invention can also be prepared starting from a compound having formula 6 according to the formula sheet.

This compound is reacted with a compound having formula 5 in which H replaced by $R_6$ and $R_6$ by H. Deprotection is then performed by replacing $R_6$ by H and reacting the product obtained with a compound having formula 3 and formula 2 consecutively. Another possibility is to react a compound having formula 6 with the product obtained by reacting a compound having formula 3 with a compound having formula 5 in which H is replaced by $R_6$ and $R_6$ by H, and reacting the compound obtained with a compound having formula 2. The intermediate steps can again be repeated m-2 times.

Instead of compounds having formula 3 according to the formula sheet, other phosphorus compounds can also be used for the preparation of the oligosaccharides according to the invention. This applies both to the methods already described and to the methods of preparation still to follow. Thus, phosphorus compounds having three reactive groups, such as $PCl_3$ or salicylchlorophosphine, can be reacted with compound 2 or 5 according to the formula sheet, then the product obtained is hydrolyzed to the corresponding phosphonate which, after activation with an activating reagent, such as pivaloyl chloride, is treated with compound 5 or 2 according to the formula sheet.

After reaction of a compound having formula 3 according to the formula sheet with compound 2 or 5 according to the formula sheet, the product thus formed may also be hydrolysed—with removal of the free reactive group left over and the permanently protecting group (which is in this case a temporarily protecting group)—to the corresponding phosphonate which, after activation with an activating reagent, is reacted with compound 5 or 2 according to the formula sheet.

If A in formula 3 is nothing and the phosphorus compound thus has a free electron pair or if, during the preparation of the oligosaccharides according to the invention, phosphorus compounds are formed which are not completely oxidized, an oxidation should be performed, for example with $I_2$/pyridine or tert.butylperoxide in order to obtain the corresponding phosphate.

Another method of preparing oligosaccharides according to the invention is by means of so-called block synthesis. In this case, fairly large fragments of the desired oligosaccharide are prepared separately and then bonded to each other. Yet another method is to prepare a fairly large fragment and to deprotect one part of the fragment obtained at a different site from the other part, as a result of which both parts can be joined to each other. The invention according to the present application therefore also relates in particular to a method for preparing oligosaccharides according to the present invention which is characterized in that 1) a compound having formula 2according to the formula sheet is reacted with the reaction product of a compound having formula 3 and formula 5 according to the formula sheet, in which formulae, k, L, A, $R_1$, $R_2$, $R_3$ and $R_6$ have the same meaning as already described and $R_4$ is a reactive group, and that the product thus obtained is deprotected by replacing $R_6$ by a hydrogen atom, and that 2) step 1) is repeated as often as desired with the product obtained in step 1) instead of the compound according to formula 2, and that 3) step 1) if so desired, step 2) are repeated starting from a compound according to formula 2 in which $k=0$, $L=1$ and $R_1$ is a temporarily protecting group, and $R_1$ being replaced by a hydrogen atom in the last step instead of $R_6$, and that 4) the product obtained in step 1) or 2) and the product obtained in step 3) are reacted with each other and in the product thus formed $R_6$ is replaced by a hydrogen atom, and that 5) the product obtained in step 4) is reacted with a compound according to formula 6 according to the formula sheet in which $R_2$, $R_3$, $R_7$, n and q have the meaning already described, and that 6) the permanently protecting group $R_1$ or $R_7$, if present and if desired, in the product thus obtained is replaced by X or Y insofar as X or Y is not hydrogen, and that 7) the compound obtained in step 5) or 6) is deprotected by replacing the permanently protecting groups by a hydrogen atom.

This method of preparation can also be performed by using a compound having formula 6 in step 3) instead of a compound having formula 2 while making use of the reaction product of a compound having formula 3 and formula 5.

This method of preparation can also be performed starting from a compound having formula 6 analogously to what has already been described in that respect.

The invention also relates to a method for preparing oligosaccharides according to the present invention characterized in that 1) a compound having formula 2 according to the formula sheet is reacted with the reaction product of a compound having formula 3 and having formula 5 according to the formula sheet in which A, $R_2$, $R_3$ and $R_6$ have the meaning already described and $R_4$ is a reactive group, $k=0$, $L=0$ and $R_1$ is a protective group and the product thus obtained is deprotecting by replacing $R_6$ by a hydrogen atom, and that 2) step 1) is repeated as often as desired with the product obtained in step 1) instead of the compound according to formula 2, and that 3) a part of the product obtained in step 2) is deprotected by replacing $R_1$ by a hydrogen atom instead of $R_6$, and that 4) the products in which $R_1$ and $R_6$ have been replaced are reacted with each other after one of said products has been reacted with a compound having formula 3, and that 5) $R_6$ in the product obtained is replaced by a hydrogen atom, and that 6) the product obtained form step 5) is reacted with a compound having formula 6 according to the formula sheet in which n, q, $R_2$, $R_3$ and $R_7$ have the meaning already described, and that 7) the permanently protecting group $R_1$ or $R_7$, if present and if desired, in the product thus obtained is replaced by X or Y insofar as X or Y is not hydrogen, and that 8) the compound obtained in step 6) or 7) is deprotected by replacing the permanently protecting groups by a hydrogen atom.

This method of preparation can also be performed in reverse sequence, i.e. starting from a compound having formula 6 and ending with the incorporation required to obtain a compound having formula 2.

One more variant of these block syntheses is that, before the two blocks are coupled, the incorporation of the terminal group (by reaction with a compound according to formula 6 or formula 2) is performed in one of the blocks. The block synthesis is in particular of advantage if fairly large oligosaccharides are being prepared. The number of reaction steps can be considerably reduced in this manner. The conditions under which the blocks are bonded to each other are in principle not different from what has already been discussed above for the other methods. The methods of preparation described may suitably be performed, in whole or in part, on a solid phase.

The invention is explained by reference to the following examples.

EXAMPLES

1. Preparation of Compound Having Formula 2 According to the Formula Sheet

Starting from D-ribonolactone, 1-O-[2-benzyloxymethyl-3,5-O-(tetraisopropyldisiloxane-1,3-diyl)-β-D-ribofuranosyl]-2,3,4-tri-O-benzyl-D-ribitol (compound 15 in scheme 1) was prepared via 13 intermediate products.

Compound 2 in scheme 1 was prepared from compound 1 as described in *Canadian J. Chem.* 36 (1958) 1720.

4.5 ml of allyl chloroformate in 10 ml of dry acetonitrile were added dropwise while stirring to 4 g of compound 2 and 3.5 ml of dry pyridine in 10 ml of dry acetonitrile at 0° C. Stirring was then continued for 1 hour at 0° C. Excess chloroformate was destroyed by adding ice. The reaction mixture was diluted with 100 ml of ether and washed 3 times with 50 ml of water. The organic layer was dried with MgSO₄ and concentrated under vacuum. The residue was dissolved in 10 ml of dichloromethane and filtered through a small column which was packed with 6 g of silica gel 60. The column was washed with 40 ml of dichloromethane. The filtrate and the wash liquid were combined and concentrated under vacuum. Compound 3 was crystallized from this with ether/diisopropyl ether.

5 g of compound 3 in 20 ml of dioxane were placed under a helium atmosphere. After 15 mg of tetrakis (triphenylphosphine) palladium had been added, the solution was kept for 15 min. under reflux conditions and the reaction mixture with compound 4 was concentrated.

8.6 g of compound 4, 3.5 g of sodium borohydride and 150 ml of dry tetrahydrofuran were heated to 55° C.

30 ml of methanol were added in 45 min. while stirring. Stirring was then carried out for 1 hour at 55° C.

After cooling, the reaction mixture was concentrated under vacuum. The residue was coevaporated with dry methanol (3×50 ml), taken up in 100 ml of dichloromethane and washed with 100 ml of a 90% saturated solution of ammonium chloride in water. The aqueous layer was extracted with dichloromethane (2×100 ml). The combined organic layers were dried (MgSO$_4$) and concentrated under vacuum. The residue was purified by means of chromatography (elution with dichloromethane/methanol 100/0→95/5). The suitable fractions contain compound 5. 6.2 g of compound 5 were dissolved in 100 ml of acetic acid, after which 40 ml of water were added. The solution was stirred for 4 hours at 50° C. The reaction mixture was concentrated under vacuum. The residue was coevaporated with dry toluene (3×24 ml) and dry pyridine (3×25 ml) and redissolved in 40 ml of pyridine. After 7.5 g of trityl chloride had been added, the solution was stirred for 12 hours at room temperature. After 5 ml of methanol had been added, the reaction mixture was concentrated under vacuum.

The residue was coevaporated with toluene (3×25 ml) and taken up in 150 ml of dichloromethane and washed with 150 ml of 1M sodium bicarbonate solution and with 150 ml of water. The organic layer was dried (MgSO$_4$) and concentrated under vacuum. After chromatographic purification performed as in the previous step, compound 6 was obtained. 7.3 g of compound 6 were dissolved in 40 ml of dry N,N-dimethylformamide, after which 2 g of sodium hydride were added in small portions. The stirred reaction mixture was cooled to 0° C. and 6.2 ml of benzylbromide in 10 ml of dry N,N-dimethylformamide were added dropwise in 30 min. Stirring was continued for a further 30 min. at 0° C. and then for 12 hours at room temperature. The 10 ml of methanol were slowly added and the reaction mixture concentrated under vacuum. The residue was taken up in 150 ml of ether and washed three times with 50 ml of H$_2$O. The organic layer was dried (MgSO$_4$) and concentrated under vacuum. Chromatographic purification of the concentrate (elution with hexane/dichloromethane 2/1 (400 ml) and 1/1 (400 ml), followed by dichloromethane) and evaporation of the correct fractions yielded compound 7. 8.5 g of compound 7 were dissolved in 135 ml of acetic acid and 15 ml of water and heated for 90 min. at 80° C. The solution was concentrated under vacuum. The residue was taken up in ether and washed with water (50 ml) and 1M sodium bicarbonate solution (2×50 ml). The organic layer was dried (MgSO$_4$) and concentrated under vacuum. 10 ml of dichloromethane/hexane 1/1 were added to the residue and filtration was performed. The filtrate was purified chromatographically (elution with 400 ml of chloroform/hexane 1/1, 400 ml of dichloromethane and dichloromethane/methanol 98/2), after which compound 8 was obtained. 3.4 g of compound 9, which was brought, and 3.1 g of compound 8 were dried by coevaporation with dioxane (3×50 ml) and then dissolved in 50 ml of dry 1,2-dichloroethane. Molecular sieves (4 Å, 10 g of activated pellets) were added and the mixture was stirred at room temperature for 90 min. under a stream of nitrogen. Then 3×30 μl of trimethylsilyl trifluoromethanesulphonate were added at intervals of 1 hour. 1 hour after the last addition. 100 μl of triethylamine were added; the molecular sieves were removed by filtration and washed with chloroform and toluene. The filtrate and the wash liquid were combined and concentrated under vacuum. The residue was purified chromatographically (elution with toluene/acetone 100/0→98/2). Compound 10 was obtained from the correct fractions. 5 g thereof were dissolved in 25 ml of dry dioxane; then 25 ml of dry methanol and 1.25 ml of 1M sodium methoxide in methanol were added. The reaction mixture was stirred for 4 hours at room temperature. After 0.25 ml of 1M sodium methoxide in methanol had been added, stirring was performed for a further hour. Then 1.25 g of Dowex 50 WX4 (H$^+$ form) were added and removed again after 30 min. by filtration and washed with methanol and chloroform. The filtrate and the wash liquid were combined and concentrated under vacuum. Chromatographic purification (elution with dichloromethane/methanol 100/0→95/5) yielded compound 11, of which 2.4 g were concentrated twice in 20 ml of dry pyridine. Then 20 ml of dry pyridine were added. The solution obtained was stirred under a nitrogen atmosphere at 0° C. and 1.4 ml of 1,3-dichloro-1,1,3,3-tetraisopropyldisiloxane were added dropwise in 15 min. Then stirring was carried out for 1 hour at room temperature. The reaction mixture was concentrated under vacuum and coevaporated with toluene (3×20 ml). The residue was taken up in 75 ml of diethyl ether and washed with 1M KH$_2$PO$_4$ (3×50 ml) and 1M NaHCO$_3$ (3×50). The organic layer was dried (MgSO$_4$) and concentrated under vacuum. After chromatographic purification (elution with dichloromethane/acetone 100/0→98/2), compound 12 was obtained, of which 1.49 g were concentrated twice from 5 ml of acetonitrile. Then 4.5 ml of acetonitrile were added. The solution was stirred under a nitrogen atmospheric at 50° C. and 1.35 ml of dry N,N-diisopropylethylamine and 0.5 ml of benzyloxymethylchloride were added in succession. After 2 hours, 0.25 ml of benzyloxymethyl chloride were added and then stirring was carried out for a further hour. The 2 ml of dry methanol were added at 50° C. After cooling, the reaction mixture was concentrated under vacuum. The residue was taken up in 40 ml of diethyl ether and washed with 1M KH$_2$PO$_4$ (3×20 ml) and 1M NaHCO$_3$ (20 ml). The organic layer was dried (MgSO$_4$) and concentrated under vacuum. After chromatographic purification (elution with hexane/ethyl acetate 10/0→9/1), compound 13 was obtained. Compound 13 (1.32 g) was dissolved in 4 ml of tetrahydrofuran. The solution was degassed 3 times and placed under helium. 1,5-cyclooctadienebis(methyldiphenylphosphine)-iridium hexafluorophosphate (2-3 mg) were added, after which the solution was again degassed 3 times and placed under helium. A stream of H$_2$ was passed over the solution for 2 min., after which it was again degassed and placed under helium. After 4 hours the reaction mixture was concentrated under vacuum. The compound 14 thus obtained was dissolved in acetone and water (1.2 g in 15 ml and 1 ml respectively). Then 300 mg of HgO and 375 mg of HgCl$_2$ were added and the suspension was stirred for 30 min. at room temperature. The HgO was removed by filtration and washed. The filtrate and the wash liquid were combined and concentrated under vacuum. The residue was taken up in 75 ml of diethyl ether and washed with 40 ml of a 50% saturated KI solution (3×), 40 ml of a 1% NaHSO$_3$ solution and 40 ml of 1M NaHCO$_3$. The organic layer was dried (MgSO$_4$) and concentrated under vacuum.

After chromatographic purification (elution with hexane/ethyl acetate 9/1→7/3), 0.97 g of pure compound 15 were obtained; Rf=0.34 (hexane/ethyl acetate 7/3), [α $_D^{20}$ = +39° (c 1.0—CHCl$_3$).

2. Preparation of Compound Having Formula 5 According to the Formula Sheet

Starting from compound 14 in scheme 1, compound 17 was prepared according to scheme 2.

Compound 14 (425 mg) was concentrated from 2 ml of dry dioxane (2×) and dissolved in 2.2 ml of 0.5M tetra-n-butylammonium fluoride in dioxane. After it had stood for 30 m, at room temperature, the solvent was evaporated off under vacuum. 25 ml of 1M NaHCP$_3$ were added to the residue and the mixture was extracted with 25 ml of dichloromethane (3×). The combined extracts were dried (MgSO$_4$) and concentrated under vacuum. After chromatographic purification (elution with dichloromethane/methanol 100/0→98/2) and concentration under vacuum of the correct fractions, 239 mg of a product was obtained which contained 200 mg of compound 16. This product was concentrated twice from 2.5 ml of dry pyridine and then dissolved in 2.5 ml of dichloromethane. After 65 μl of N,N-diisopropylethylamine and 90 μl of tert.butyldiphenylsilyl chloride had been added, the reaction mixture was stirred for 12 hours at room temperature. After 65 μl of N,N-diisopropylethylamine and 90 μl of tert.butyldiphenylsilyl chloride had been added stirring was carried out for a further 24 hours. 0.5 ml of methanol were then added and concentration was then carried out under vacuum. The residue was taken up in diethyl ether (25 ml) and washed with 1M KH$_2$PO$_4$ (3×10 ml) and 1M NaHCO$_3$ (10 ml). The organic layer was dried (MgSO$_4$) and concentrated under vacuum. Chromatographic purification (elution with hexane/ethyl acetate 10/0→7/3) yielded 254 mg of compound 17; Rf=0.41 (hexane/ethyl acetate 7/3) and [α]$_D^{20}$ = −24.8° (c=1.0 CHCl$_3$).

3. Preparation of Compound Having Formula 3 According to the Formula Sheet 2-chlorophenyl-0,0, -bis(1-benzotriazolyl) phosphate was prepared according to I.R.L. Press, Oxford, U.K. (1984) 153–183. This compound is hereinafter termed compound 18.

4. Preparation of Compound Having Formula 1 According to the Formula Sheet

An oligosaccharide according to the present invention was prepared according to scheme 3.

229 mg of compound 15 and 254 mg of compound 17 were separately concentrated from 2.5 ml of pyridine (3×, the last time to a volume of 1 ml). Then 1.46 ml of a 0.2M solution of compound 18 in dioxane were added to compound 17, after which the solution was stirred for 30 min. at room temperature. This solution was added to a mixture of compound 15 and 50 μl of N-methylimidazole under anhydric conditions. After it had been stirred for 2 hours at room temperature, the solution was diluted with 50 ml of diethyl ether and washed with 1M triethylammonium bicarbonate (2×25 ml), 1M KH$_2$PO$_4$ (25 ml) and 1M triethylammonium bicarbonate (25 ml). The organic layer was dried (MgSO$_4$) and concentrated under vacuum. Chromatographic purification (elution with hexane/ethyl acetate 10/0→8/2) yielded 368 mg of compound 19 (n=1), which was then treated with HgO/HgCl$_2$ as described for the preparation of compound 15. After chromatographic separation (elution with hexane/ethyl acetate 9/1→7/3), compound 20 (n=1) was obtained.

Compound 21 (0.22 mmol), prepared by reaction of the pentachlorophenyl ester of benzyloxycarbonyglycine and 3-amino-1-propanol in dioxane (room temperature, 1 hour) was phosphorylated with compound 18 (1.1 ml of a 0.2M solution in dioxane). The solution was added to a mixture of 296 mg of compound 20 (n=1) and 20 μl of N-methylimidazole. After stirring for 2 hours at room temperature, a solution, obtained by phosphorylating 0.30 mmol of compound 21 with 1.5 ml of a 0.2M solution of compound 18 in dioxane (30 min.), was again added to the reaction mixture. After 2 hours, compound 22 (n=1) was obtained by means of a washing procedure as described in the preparation of compound 19 (n=1) and a chromatographic purification (elution with chloroform/acetone 100/0→95/5).

Compound 22 (n=1) (285 mg) was deprotected by the following steps in succession:

Removal of 2-chlorophenyl groups by reaction with synpyridine-2-carboxaldoxime and $N^1, N^1, N^3, N^3$-tetramethylguanidine in tetrahydrofuran for 48 hours at room temperature;

Removal of the 1,1,3,3,-tetraisopropyldisiloxane-1,3-diyl and the tert.butyldiphenylsilyl group by reaction in dioxane with tetra-n-butylammonium fluoride for 16 hours at room temperature;

Removal of the benzyloxycarbonyl, the benzyloxymethyl and the benzyl groups by hydrogenolysis in tert.butanol/water (24 h.) and water (24 h.), successively, in the presence of 10% Pd/C (600 mg) and glycinamide.

After removal of the catalyst by filtration, washing of the filtrate (3×) with chloroform, evaporating the chloroform off, freeze-drying, gel filtration over Sephadex G-25 (elution with 0.01M triethylammonium bicarbonate pH 7), freeze-drying of the sugar-positive fractions, the material obtained was passed through a Dowex 50 WX4 (Na$^+$ form) column in water. After freeze-drying, 51 mg of the solid compound 23 (n=2) was obtained.
$^{31}$P NMR:

δ 1.54 and 0.74. $^1$H NMR (ref. HDO, 4.65 ppm): δ 4.90 (s,1 H); 4.86 (s, 1 H); 4.5–4.4 (m, 8 lines, 1 H); 3.21 (t, —NH—CH$_2$—CH$_2$—, spacer); 1.71 (t, —CH$_2$-CH$_2$—CH$_2$, spacer).

$^{13}$C NMR (external reference tetramethylammonium chloride δ 56.2): δ 167.8 (s), 107.7 (s, C-1 Ribf), 107.5 (s, C-1 Ribf), 83.5 (s, CH), 82.8 (d, CH, J$_{CP}$ 5.8 Hz), 75.2 (s, CH), 75.1 (d, CH, J$_{CP}$ 3.4 Hz), 74.6 (br s, CH, J$_{CP}$ unresolved), 72.3 (s, 2×CH), 71.8 (d, 2×CH, J$_{CP}$ 8.8 Hz), 71.4 (s, CH), 71.0 (s, 2×CH), 6.95 (s, CH$_2$), 6.93 (s, CH$_2$), 67.5 (d, CH$_2$, J$_{CP}$ 4.4 Hz), 67.3 (d, CH$_2$ J$_{CP}$ 4.4 Hz), 64.4 (d, CH$_2$, J$_{CP}$ 5.9 Hz), 63.4 (s, CH$_2$), 63.2 (s, CH$_2$). 41.3 (s, CH$_2$ Gly), 37.2 (s, CH$_2$), 30.0 (d, CH$_2$, J$_{CP}$ 7.3 Hz).

FAB MS (fast atom bombardment mass spectrometry) revealed m/z 823 [compound 23, n=2, —Na]$^-$ as the most abundant signal in the high-mass region.

5. Preparation of Compound 23 (n=3)

Compound 20 (n=1) (0.46 mmol) was added to a solution obtained by phosphorylating 0.56 mmol of compound 17 with 3 ml of a 0.2M solution of compound 18 in dioxane/pyridine for 30 min. After 3 hours, 0.36 mmol of compound 19 (n=2) was obtained. Analogously to the procedure already described above, 0.30 mmol of compound 20 (n=2) was then prepared and, starting from 0.15 mmol of compound 20 (n=2), 478 mg of compound 22 (n=2) were obtained. From this compound, 45 μmol were deprotected to compound 23 (n=3). Yield 22 mg; $^{31}$p NMR: δ1.66 and 0.85 (two overlapping signals); $^1$H NMR in D$_2$O (ref. HDO, δ 4.65): 4.92 (s, 2 H); 4.88 (s, 1 H); 4.55–4.42 (m, 2 H); 3.25 (t, 2 H, spacer —NH—CH$_2$—CH$_2$—): 1.74 (t, 2 H, spacer —CH$_2$—CH$_2$—CH$_2$—); $[α]_D^° = -30.1°$ (c=1.0, H$_2$O).

6. Preparation of Immunogens

Immunogens were prepared by coupling compound 23 (n=2) and compound 23 (n−3), (see scheme 3) to tetanustoxoid (TT) and *Haemophilus influenzae* type b outer-membrane protein (MP) according to scheme 4.

First the oligosaccharides 23 (n=2,3) were modified by reacting the terminal amino group with N-succinimidyl S-acetylmercaptoacetate, which produced compound 24 (n=2 or 3). 2-Pyridyldithio (PDP) groups were introduced on the proteins by reacting the ε-NH$_2$ groups of the lysines with N-succinimidyl 2-pyridyldithiopropionate (SPDP). Compounds 24 and 25 were added in a buffer (pH 6.1). The S-acetyl group of the oligosaccharide component was split off by adding hydroxylamine, as a result of which a free —SH group is produced. The thio 26 then reacts with a PDP group on the protein to form compound 27. The extent of incorporation of the oligosaccharide was determined by a differential UV measurement of the quantity of 2-thiopyridione liberated ($Δε343=8,000M^{-1}$).

MATERIALS

Solutions of tetanus toxoid (10 mg/ml() and H. Influenzae outer-membrane protein (2.5 mg/ml in 0.14M NaCl +0.1% Zwittergent 3-14). N-succinimidyl S-acetylmercaptoacetate was prepared according to *Anal. Biochem.* 132 (1983) 68–73, SPDP was obtained from Pierce Chemical Company and Zwittergent 3–14 (N-tetradecyl-N,N-dimethyl-3-ammonio-1-propane sulphonate) from Calbiochem. N-ethylmorpholine and dimethylacetamide were distilled from fluoroinitrobenzene.

Buffer A:2M N-ethylmorpholine/HCl pH 8.5
Buffer B:0.01M triethylammonium bicarbonate pH 7.0
Buffer C:0.1M sodium phosphate +0.005M EDTA (disodium ethylenediaminetetraacetate dihydrate) pH 6.1
Buffer D:0.1M sodium phosphate pH 7.8.
PD-10 column: Pharmacia prepacked Sephadex G-25M disposable column (volume 9.1 ml, height 5 cm).
G-25 column:100×1.0 cm Pharmacia Sephadex G-25 (superfine).

PREPARATION OF COMPOUND 24

19.8 mg (21.4 μmol) of the triethylammonium form of compound 23 (n=2) were dissolved in 0.21 ml of buffer A, after which 25 mg of N-succinimidyl S-acetylmercaptoacetate in 0.85 ml of dimethylacetamide were added. The homogenous reaction mixture was kept for 1 hour at room temperature. Then acidification was carried out by adding acetic acid (100 μl). The sugar material was precipitated by adding 5 ml of acetone. The syrupy precipitate was centrifuged off, dissolved in a small volume of buffer B and purified via a G-25 column using this buffer as eluant. The sugar-containing fractions were combined and freeze-dried. The product obtained was freeze-dried two more times from water and then dissolved in 0.50 ml of buffer C. The product contained 11.5 μmol of compound 24 (n=2). 11 mg of compound 23 (n=3) were converted into compound 24 (n=3) in an identical manner. The product contained 4.2 μmol of compound 24 (n=3).

PREPARATION OF COMPOUND 25

A PD-10 column was equilibrated with 25 ml of buffer D. Then 1.50 ml (15 mg, approx. 100 nmol, molecular weight approx. 150,000) of a TT solution was introduced and eluted with buffer D. 4.5 mg of SPDP in 0.45 ml of ethanol were added to the solution of TT ion buffer D (elution volume 2.5–6.0 ml) thus obtained. After reacting for 1 hour at room temperature, the reaction mixture was introduced into the G-25 column and eluted with buffer C. The protein-containing fractions were combined and diluted to 20 ml (protein concentration approx. 5 nmol/ml) with buffer C in which a pinch of sodium azide had been dissolved. 3.0 ml of this solution was treated under helium with 1.0 μmol of dithiothreitol. After being left to stand for 24 hours at room temperature, $ΔE_{343}$ was=1,648 (reference: untreated PDP-TT). Since $Δε,_M=8,000$, the content of 2-thiopyridone is 206 nmol/ml. The incorporation was 41 PDP/TT.

15 mg of TT was treated with 1.0 μmol of SPDP in an identical manner. The G-25 fraction was diluted to 15 ml. Incorporation: 4.5 PDP/TT.

analogously, 3.75 mg (approx. 95 nmol, molecular weight approx. 40,000) of MP were twice transferred to 3.5 ml of buffer D. The protein was treated with respectively 14.4 and 0.4 μmol of SPDP.

After gel filtration via G-25, the protein fraction was diluted to 15 ml (protein concentration approx. 5.25 nmol/ml). Because the MP is very hydrophobic, 0.1% of Swittergent 3–14 was in this case added to the buffers C and D. Incorporation: approx. 4.9 and approx. 1.3 PDP/MP.

PREPARATION OF COMPOUND 27

43 μl (1.0 μmol) of the solution obtained earlier of compound 24 (n=2) in buffer C were added to 3.0 ml (1 mg/ml) of 4.5 PDP/TT, 4.5 ml (0.75 mg/ml) of 41 PDP/TT, 4.5 ml (0.25 mg/ml) of 1.3 PDP/MP and 4.5 ml of 4.9 PDP/MP (C-25 fractions in buffer C, see above). The solutions were deaerated with helium. Then 10 μl of 0.2M hydroxylamine pH 6.15 were added. After overnight reaction at room temperature, the quantity of 2-thiopyridone formed was determined. The expected quantity of thiopyridone was split off the proteins 4.5 PDP/TT, 1.3 PDP/MP and 4.9 PDP/MP and a corresponding quantity of compound 27 was therefore formed. An average of 20 molecules of compound 26 were coupled to the 41 PDP/TT. After an additional quantity of compound 24 (n=2) had been added, the degree of saccharide-incorporation remained unchanged. To an analogous conjugate which, after a shorter reaction time, contained 17 molecules of dimer, 1 μmol of cysteine was added. The total quantity of thiopyridone expected was then rapidly formed.

Compound 24 (n=3) was used in an analogous manner for the preparation of trimer-protein conjugates according to compound 27.

In summary, the following conjugates were made:
1.3 and 4.9 dimer and timer/MP
4.5 dimer and trimer/TT
20 dimer/TT (with 21 residual PDP groups).

17 dimer/TT (without residual PDP groups as a result of post-treatment with cysteine)

13 trimer/TT (28 residual PDP groups).

The antigenicity of these conjugates was measured and compared with that of native polysaccharide of HIB (Ca-salt), human polysaccharide vaccine and the homologous antigen (=polysaccharide/MP) which produces the mouse antibodies. The substances to be tested were mixed in a two-fold dilution series with a fixed quantity of antiserum. After incubation for 1 hour at room temperature, the titre of the residual free antibodies was determined in a direct ELISA inhibition test. The results are as follows:

| Conjugate | Concentration (µg/ml) | % inhibition |
|---|---|---|
| 1.3 dimer/MP | 10 | 45 |
| 1.3 trimer/MP | 10 | 86 |
| 4.9 dimer/MP | 10 | 49 |
| 4.9 trimer/MP | 10 | 81 |
| 4.5 dimer/TT | 10 | 21 |
| 4.5 trimer/TT | 10 | 56 |
| 20 dimer/TT | 10 | 19 |
| 17 dimer/TT | 10 | 20 |
| 13 trimer/TT | 10 | 53 |
| native polysaccharide (Ca-salt) | 10 | 91 |
| human polysaccharide vaccine | 10 | 90 |
| homologous antigen (tyraminated) polysaccharide) | 10 | 12 |

As is evident from this, the dimer conjugates exhibit a considerable bonding to the antibodies, although said bonding is markedly lower than that of the native polysaccharide. The ability of the native polysaccharide to bond to antibodies can be almost equalled by the trimer conjugates.

7. PREPARATION OF VACCINE

A trimer-oligosaccharide (compound 23, n=3) was bonded to tetanus toxoid with glutardialdehyde by mixing a 10-100-fold excess (on a molar basis) of the trimer with tetanus toxoid and by adding glutaric dialdehyde 3× in excess with respect to the ligand at intervals of 1 hour. After the reaction mixture had been allowed to stand for 5 hours at room temperature, a 20-fold excess (with respect to the ligand) of glycine was added. After 1 hour at room temperature, NaCNBH$_3$ was added. After 5 hours at room temperature the reaction mixture was dialysed. Starting from 2.4 mmol of trimer, 120 µmol of conjugate was obtained, 3 trimers being incorporated per tetanus toxoid (3 trimer/TT), the trimer:TT weight ratio being 0.1:3.

Mice were injected with a conjugate of *Haemophilus influenzae* type b polysaccharide and *Haemophilus influenzae* type b outer-membrane protein coupled by means of adipinedihydrazide (PS-MP). The weight ratio of protein and polysaccharide in the conjugate was 1:1. The dose per injection was 5 µg of conjugate. Injection was repeated 3 and 5 weeks after the first injection. After 6 weeks the IgG titre was determined and adjusted to 100.

Other mice were injected with 3.12 µg of the 3-trimer/TT conjugate. After 4 weeks, this injection was repeated and after 6 weeks, the IgG titre was determined, which was 36 with respect to the PS-MP titre adjusted to 100.

The strong immunogenicity of the 3 trimer/TT conjugate may be evident from the fact that approximately ⅓ of the IgG titre which was obtained by injecting 7.5 µg of polysaccharide was achieved with only 0.25 µg of oligosaccharide. With 1/30 of the weight, ⅓ of the effect was obtained. In addition, the injection with the trimer was repeated only once, while that with the polysaccharide was repeated twice.

We claim:

1. A synthetic Oligosaccharide which comprises D-ribose, D-ribitol and phosphate in any order repeated m times, wherein m is an integer from 2 to 20.

2. Oligosaccharide according to claim 1, having the formula:

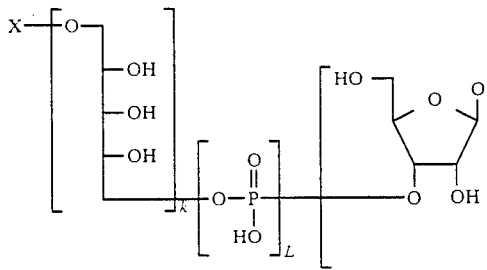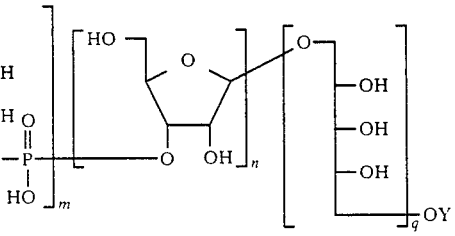

(formula I)

where
k=0 or 1 when L=1
k=0 when L=0,
L=0 or 1,
m=an integer from 2 to 20, with the proviso that m is 1 when k, L and n=1 or when L, n and q=1,
n=0 or 1,
q=0 or 1 when n=1,
q=0 when n=0,
X=hydrogen, a reactive group which is capable of forming a bond with a carrier, or a group containing a hydrophobic chain at the unbonded end, or the terminal group XO— is replaced by the reactive group H$_2$N— or HS—, and
Y=hydrogen, a reactive group which is capable of forming a bond with a carrier, or a group containing a hydrophobic chain at the unbonded end, or the terminal group —OY is replaced by the reactive group —NH$_2$ or —SH, with the proviso that Y=hydrogen when X≠hydrogen and that X=hydrogen when Y≠hydrogen, and salts thereof.

3. Oligosaccharide according to claim 2, wherein m=2,3,4,5 or 6.

4. Oligosaccharide according to claim 2, wherein X=hydrogen and Y≠hydrogen.

5. Oligosaccharide according to claim 2, wherein Y=hydrogen and X≠hydrogen.

6. Oligosaccharide according to claim 2, wherein the reactive group is a group which contains one of the following reactive functions:

—NH₂, —SH,

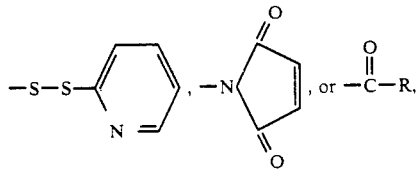

where R= —OH, —N₃, —O-alkyl (C₁₋₁₂),

—OC₆F₅, —H, —Br, —Cl or

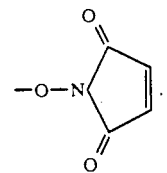

7. Oligosaccharide according to claim 2, wherein X or Y is a group with an alkyl group containing 12-24 carbon atoms at the unbonded end.

8. Oligosaccharide according to claim 2, wherein the oligosaccharide is homogeneous.

9. A process for preparing an oligosaccharide according to claim 1, comprising replacing the protective groups in an oligosaccharide by a hydrogen atom, said oligosaccharide comprising the structure (D-ribose-D-ribitol-phosphate)$_m$, (D-ribitol-phosphate-D-ribose)$_m$ or (phosphate-D-ribose-D-ribitol)$_m$, wherein m=an integer from 2 to 20 and replacing the hydrogen atom in the free hydroxy groups by a protecting group.

* * * * *